United States Patent [19]  
Michel et al.

[11] Patent Number: 4,969,874  
[45] Date of Patent: Nov. 13, 1990

[54] INFUSION DEVICE

[75] Inventors: Peter Michel, Burgdorf; Hans Müller, Gunten, both of Switzerland

[73] Assignee: Disetronic Ag., Burgdorf, Switzerland

[21] Appl. No.: 297,859

[22] PCT Filed: May 18, 1988

[86] PCT No.: PCT/CH88/00092

§ 371 Date: Nov. 25, 1988

§ 102(e) Date: Nov. 25, 1988

[87] PCT Pub. No.: WO88/09187

PCT Pub. Date: Dec. 1, 1988

[30] Foreign Application Priority Data

May 18, 1987 [CH] Switzerland ............... 01905/87  
Jul. 27, 1987 [CH] Switzerland ............... 02851/87

[51] Int. Cl.$^5$ ............................................. A61M 37/00  
[52] U.S. Cl. .................................. 604/140; 604/141; 604/143; 604/145  
[58] Field of Search ............... 222/396, 389; 604/140, 604/141, 143, 145–150

[56] References Cited

U.S. PATENT DOCUMENTS

| 2,545,017 | 3/1951 | Billingsley | 604/143 |
| 3,433,224 | 3/1969 | Black | 604/143 |
| 4,113,144 | 9/1978 | Hein et al. | 222/396 |
| 4,351,335 | 9/1982 | Whitney et al. | 604/143 |

Primary Examiner—Randall L. Green  
Assistant Examiner—Randy Shay  
Attorney, Agent, or Firm—Brady, O'Boyle & Gates

[57] ABSTRACT

An insert head (102) is tightly inserted in the rearward end of a commercially available ampoule (101) equipped with a plunger (100). A galvanic, gas-generating cell is arranged in the insert head (102). The plunger (100) is driven forward by the gas generated by this cell. A throttle device (103) constituted by a capillary tube is connected to the Luer's syringe (109) of the ampoule (101), the infusion fluid driven out by the plunger (100) flowing through this throttle means into a catheter (104).

13 Claims, 3 Drawing Sheets

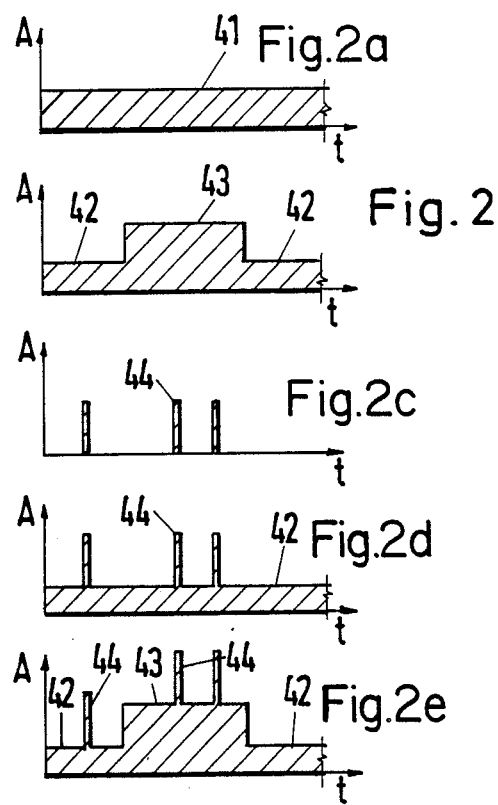
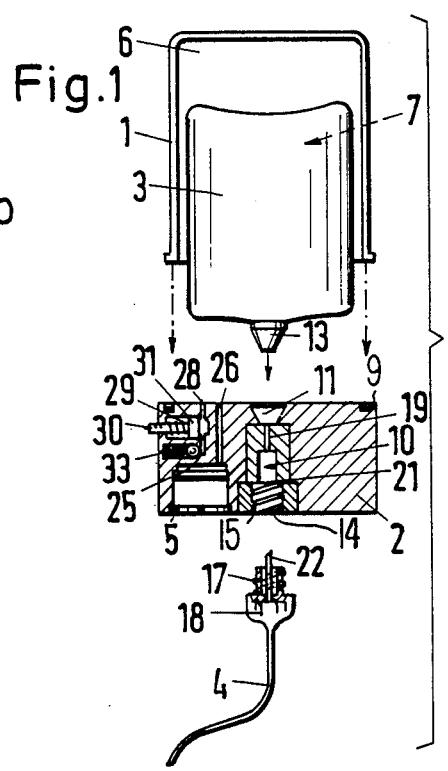
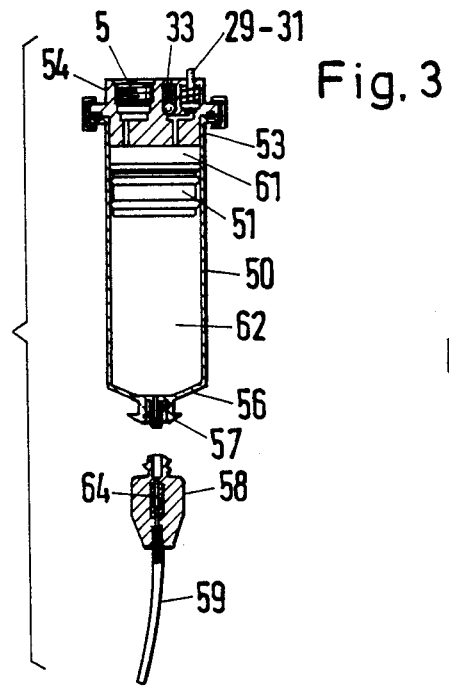
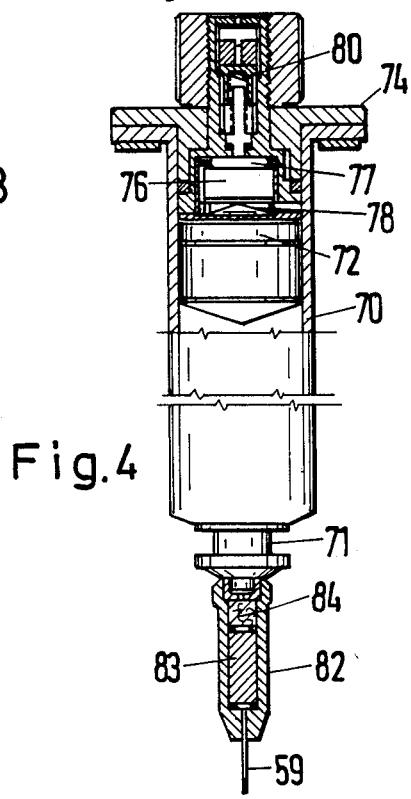

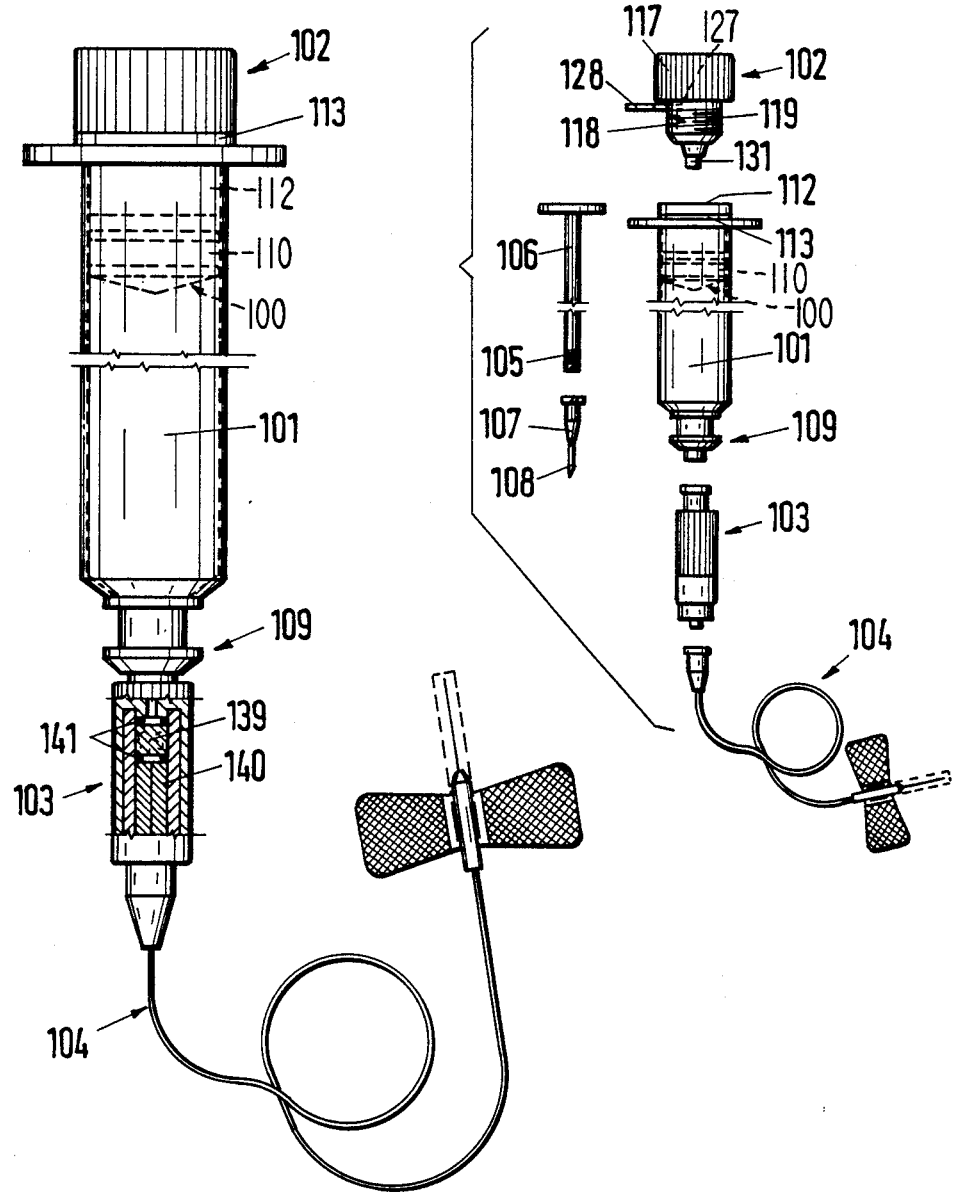

INFUSION DEVICE

The invention relates to an infusion device.

The invention is based on the object of providing an infusion device which is economical, compact, lightweight, reliable and safe in its function, simple to manipulate, operable in any position, suitable for outpatient use, and suitable also for being carried on the body of the patient.

SUMMARY OF THE INVENTION

To achieve the foregoing objects of the invention a medical infusion device is provided which uses a gas generating galvanic cell, having a load resistor connected across the galvanic cell, for activating the medical infusion device, which comprises a chamber for accommodation of a liquid to be infused into the body of a patient, this chamber having an outlet for the infusion liquid and being variable in volume by a moveable wall, which wall, on the side facing away from the chamber, is subjected to the pressure of a gas constantly being delivered by a gas generating galvanic cell under the load of a resistor. In one form of the invention, the chamber accommodating the infusion liquid and the moveable wall comprise a compressible bag-like container for the infusion liquid, the bag being connected inside a chamber of the medical infusion device into which the gas from the galvanic cell is delivered whereby the outside of the bag is subjected to the pressure of the gas which moves or collapses the flexible wall of the bag-like container to dispense the infusion liquid therefrom through the outlet. In another form of the invention, the chamber accommodating the infusion liquid is a substantially cylindrical ampoule and the moveable wall comprises a piston closing one end of the ampoule and moveable toward the infusion liquid in said ampoule, by the gas generated from a galvanic cell connected in a chamber behind the moveable wall or piston, to dispense the infusion liquid from the outlet in the opposite end of the ampoule.

BRIEF DESCRIPTION OF THE DRAWINGS

Embodiments of the invention will be described in greater detail below with reference to the drawings wherein:

FIG. 1 shows an axial longitudinal section through a first embodiment of the infusion device with a connection unit pertaining thereto, in exploded representation, FIGS. 2a-2e show schematic views, FIG. 3 is an axial longitudinal section through a second embodiment of the infusion device with an associated connection unit, in exploded view, FIG. 4 shows an axial longitudinal section through one version of the second embodiment, FIG. 5 shows an exploded view of a preferred, third embodiment of the infusion device, FIG. 6 is an illustration of the embodiment of FIG. 5 in a condition ready for operation, partially in a sectional view.

Figure 7:
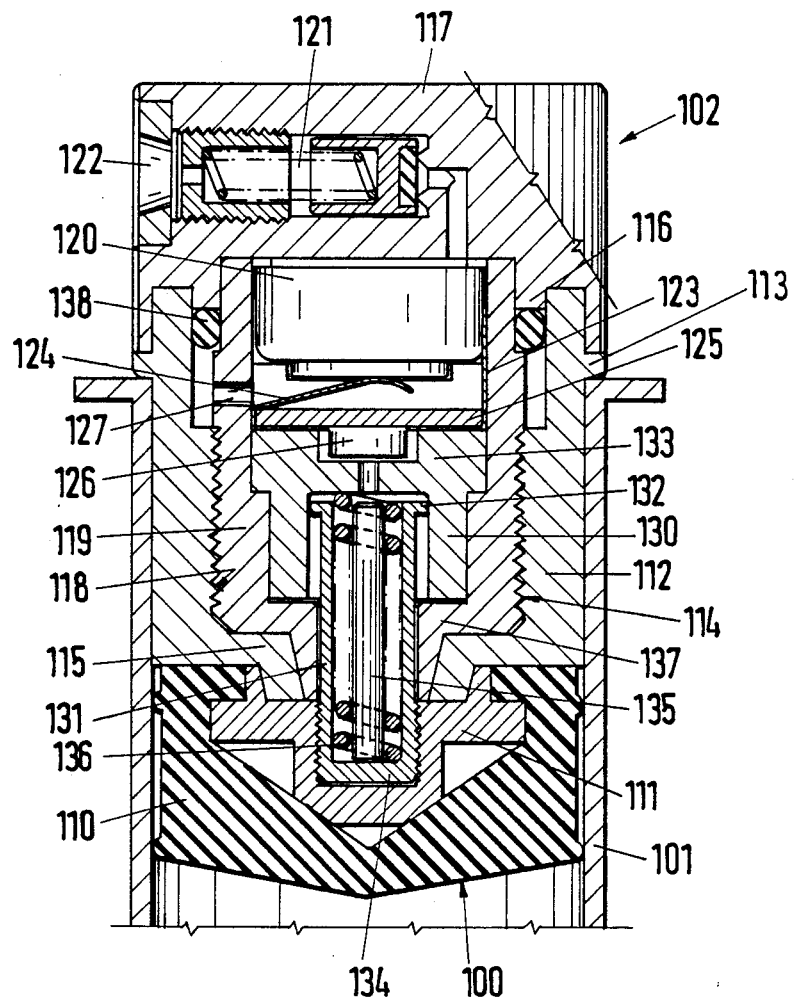
FIG. 7 is an axial longitudinal section through the insert head, introduced into the ampoule, pertaining to the infusion device ready for operation according to FIG. 6, on an enlarged scale.

The infusion device illustrated in FIG. 1 consists in its basic structure of a bipartite housing 1, 2, a compressible, bag-like container 3 for the infusion fluid, this container being arranged in the housing 1, 2 and being connectible on the outside of this housing to a hose or infusion catheter 4, and of a means 5, 33 for producing a constant excess pressure in the portion 6 of the housing space surrounding the container 3, this means consisting, in the illustrated embodiment, of a galvanic cell 5 and a pressure relief valve 33 responding at the desired excess pressure. The galvanic cell 5 is, for example, of the type known from DOS 3,532,335 and preferably has a structure corresponding to the button cell described therein, similar to the commercially available zinc/air cell particularly for use in hearing aids, but employed for the novel task, foreign to its usual purpose, of hydrogen release by short-circuiting the cell by way of a low resistance while preventing the access of air, resulting in hydrogen generation and the production of an expanding flow. The gas-generating galvanic cell 5 contains in the initial condition, (a) only electrochemically oxidizable material and a hydrogen-generating electrode and aqueous electrolyte, or (b) only electrochemically reducible material and an oxygen-generating electrode and an aqueous electrolyte, and hydrogen or oxygen is formed or produced in the pores of a gas diffusion electrode and enters the outer chamber via the ports of a hydrophobic membrane, whereas the electrolyte is retained in the interior of the cell container by the high capillary depression of this membrane. The galvanic cell 5 consists of an outer cup housing member electrode and a lid electrode closing one end of the cup and insulated therefrom by a synthetic resin seal. Active material in the form of an electrolyte-containing zinc gel, or, alternatively, in the form of a porous manganese dioxide pill is connected to and contacted by the lid electrode inside the cell. A compressible porous member can be connected between the active material and the inside of the lid electrode, wherein an additional quantity of electrolyte can be made available. An electrolyte-saturated mat is in contact with the side of the active material away from the lid electrode, and a separator, for example, in the form of an ion exchange film, separates the electrolyte-saturated mat from a gas diffusion electrode, inside and in electrical contact with the cup housing electrode. The gas diffusion electrode consists, for example, of a PTFE-bond Raney nickel powder layer which has been rolled into a nickel mesh and has a porous PTFE film toward the bottom inside of the cup. A coarse mat layer adjacent the inside bottom of the cup, serves for guiding the gas exiting from the gas diffusion electrode during operation toward a hole in the bottom of the cup housing electrode (not shown), so the gas can pass out of the galvanic cell 5 into the portion 6 of the housing space, or into the head section chamber containing the button cell or galvanic cell. The cell is under the load of a resistor (not illustrated in FIGS. 1 and 3) and delivers a constant quantity of hydrogen or oxygen per unit time, determined by the load.

Since every zinc atom releases two electrons, i.e. permits reduction of one water molecule with formation of hydrogen, proportionately 18 g. of water must be introduced into the galvanic cell 5 per 65 g. of zinc.

The housing part 1 is tank-shaped and consists of a transparent material so that the filling condition of the container 3 can be monitored and the progression of the infusion can be observed at the continuously further collapsing container 3. In the filled condition, the container 3 has a small spacing from the wall of the housing part 1. The housing part 2 forms a lid for part 1; this housing part 2 carries the container 3, is designed with the hose 4 for connecting the container 3, and holds the means 5, 33 for producing the excess pressure and additional accessories of the infusion device. Parts 1 and 2 are releasably joined, for example by a (not illustrated) screw, bayonet or clamping closure and are mutually sealed by means of a sealing ring 9.

As can be seen, the housing space is divided into two component chambers by the wall of the bag 3, one of these chambers, denoted by 6, being connected to the means 5, 33 for compressed gas generation and regulation, and the other, denoted by 7, namely the space of bag 3, serving for receiving the infusion fluid and being connectible to the hose 4. In this arrangement, the wall of the bag 3 transmits the gas pressure to the infusion fluid without the gas coming into contact with the latter.

The container part 2 is provided with a continuous opening 10. The end 11 of the passage opening 10, on the inside based on the container 1, 2, is detachably connected to a discharge nipple 13 of the container 3 (for example a plug-in or threaded connection) so that the container 3 can be exchanged after detaching the housing part 1 from the housing part 2. The other, external end 14 of the passage opening 10 is designed for connection to the infusion catheter 4, for example with an internal thread 15 for an external thread 17 of a connection member 18 of the hose 4. A constricted or throttle point 19 is formed in the passage opening 10 and a closure member 21 (for example diaphragm-type) is arranged therein, through which a hollow needle 22 of the connecting member 18 penetrates when the hose 4 is connected. The constricted zone 19 and the hollow needle 22 then limit the infusion rate, at the given excess pressure in chamber 6 and at the given viscosity of the infusion fluid. In this arrangement, the discharge nipple 13 of the container 3 must be opened prior to insertion in the internal end 11 of the passage opening, for example by cutting off a projection formed at the nipple (not shown). Also, a hollow needle (not shown) could be provided, located concentrically within the passage opening 10, this needle penetrating through the outer end of the discharge nipple 13 when the latter is inserted in the internal end 11 of the passage opening 10. However, the device can also be fashioned without the constricted or throttle site 19 so that the hollow needle 22 is pushed through the outer end of the discharge nipple 13 in order to connect the hose 4 to the container 3. In this case, the hollow needle 22 also takes over the function of the narrowed or throttle zone 19.

The galvanic cell producing the gas is exchangeably located in a cavity 25 formed in the housing part 2; this cavity is in communication with chamber 6 through a duct 26. The duct 26 suitably terminates (in a deviation from the schematic view) closely beside the cylindrical jacket of the housing part 1 into the chamber 6 so that the bag-like container 3 does not impede efflux of the gas. This holds true correspondingly for a duct 28, to which are connected a pressure gauge with a piston 31 under the bias of a spring 29 and connected to a pin 30 provided with a graduated scale, and the pressure relief valve 33 which maintains the gas pressure constant in chamber 6. The resultant gas loss can be tolerated because commercial galvanic cells of this type deliver, when cooperating with the relief pressure valve 33, an amount of gas adequate at least for an infusion. The pressure gauge 29-31 and the valve 33 are arranged in housing part 2.

Instead of the galvanic cell 5, it is also possible to utilize a compressed gas cartridge exchangeably provided in the housing part 2. A cartridge is suitable, in particular, which has a system (known from pocket-size lighters) of communicating chambers containing, in part, a liquid of low boiling point and, in part, the vapor of such liquid, wherein entrance of the liquid into a vapor chamber is prevented. The liquid is to be chosen so that its vapor pressure corresponds to the excess pressure desired in chamber 6. In this arrangement, a hollow needle terminating into the duct 26 is to be located in the space accommodating the cartridge, this needle penetrating into the vapor chamber of the cartridge protected from the entrance of the liquid when the cartridge is inserted in the device. When using a cartridge that contains solely gas, the corresponding hollow needle would have to be connected to the duct 26 by means of a reducing valve in case the content of the gas cartridge is not enough for maintaining the gas pressure, held constant by the pressure relief valve 33, for an adequately long period of time.

For generation of the excess pressure, a pneumatic pump, e.g. a piston pump, could also be utilized, driven by a battery-supplied motor, this motor being switched on and off by a regulating valve when the pressure in the sectional chamber 6 of the housing falls below or, respectively, exceeds the desired pressure.

An essentially constant release rate of the infusion fluid can be administered by means of the device once the gas pressure has been built up. However, it is likewise possible to administer a release rate that varies stepwise and, additionally, respectively one bolus, by changing the gas pressure in chamber 6 and/or the flow resistance of the constricted or throttle site 19. For changing the gas pressure, the load resistor connecting the anode and cathode of the galvanic button cell 5 can be varied, by activating, for example, a semiconductor element, suitably a transistor, acting as the load resistor. Alternatively, if a compressed gas cartridge that contains only a gas is utilized, the reducing valve can be fashioned to be adjustable. Also program control can be provided for the pressure. In case the pressure generator is a galvanic cell with a transistor as the load resistor, then electric control can be employed in place of pressure regulation by means of the pressure relief valve, a pressure sensor which is, for example, piezoelectric regulating the transistor.

Instead of exerting control according to a program, the flow resistance of the constricted or throttle point 19 and/or the pressure in chamber 6 can also be regulated by a patient-monitoring system in dependence on the respective condition of the patient (e.g. pulse, blood sugar).

FIG. 2 illustrates several possibilities of this kind in a merely schematic representation; in reality, delivery is not immediately initiated at the beginning of gas generation but rather occurs with a delay and the desired release rate is attained only after one-half to one hour, and the release rate changes, upon changing of the gas pressure, in a gradual way rather than abruptly. FIG. 2a shows a constant delivery rate (A) 41 without additional bolus; FIG. 2b shows a release rate 42, 43, 42 that changes in a stepwise fashion; FIG. 2d illustrates a constant delivery rate 42 with a bolus 44 repeated at irregular intervals. FIG. 2e shows an application wherein the bolus 44 is repeatedly superimposed upon the release rate 42, 43, 42 that changes stepwise. According to FIG. 2c, only the bolus 44 is administered in timed repetition. For this purpose, a valve (not shown) is to be arranged in series with the constricted or throttle site 19, or this site 19 is to be replaced by a valve that would have to be opened for the uses according to FIGS. 2a, 2b, 2d, and 2e, but which would have to be closed for the usage according to FIG. 2c.

The infusion device according to FIG. 3 consists in its basic structure of a cylinder 50 made of a transparent material wherein a plunger 51 is disposed to be readily displaceable. The cylinder 50 is sealed at one end 53 by a lid 54. The other cylinder end 56 tapers conically and is provided with an outlet extension 57 formed at one end of a hose 59 for connecting a connection member 58; this hose is to be employed as an infusion catheter or is equipped at the other end (not shown) with an infusion needle. The cylinder 50 with the tapered portion 56 and the outlet extension 57 and the plunger 51 (without piston rod) can be part of a plunger-type syringe commercially available for medical purposes.

The lid 54 is detachably connected to the cylinder 50 and contains a device for pressure gas generation, for example a galvanic cell 5, a pressure indicator 29-31, and a pressure relief valve 33, denoted in FIG. 3 by the same reference numerals as in FIG. 1, and to which the above-description applies analogously.

As can be seen, the cylinder chamber is separated by the plunger 51 into two component chambers, one of which, 61, is connected to the device 5 for compressed gas generation, and the other of which, 62, serves for receiving the infusion fluid and is connectible to the hose 59. In this arrangement, the plunger 51 transmits the gas pressure to the infusion fluid without the gas coming into contact with this fluid.

The plunger 51 can be designed on its side facing the lid 54 for the engagement of an auxiliary means with which the plunger, with the lid 54 being removed, can be pulled upwards in the position of the device shown in FIG. 3, for filling the device, the infusion fluid being taken in at the outlet connection 57. For this purpose, the plunger 51 can be provided with an indentation bridged by a web where a pair of tweezers or a hook can engage, or the indentation can be shaped for introduction of a key which latter can be connected with the plunger 51, by turning, in a tension-proof manner, or it can be provided with a threaded bore into which can be threaded a threaded pin with a handle for retracting the plunger 51. For this type of filling or refilling the device, the displacement of the plunger 51 is suitably limited by a stop (not shown) at the cylinder end 53.

In order to expel air from the space 62 (and optionally from the connected hose 59), the device—in accordance with the usual procedure when using plunger-type syringes—can be held with the outlet connection 57 upwardly and pressure can be exerted by hand on the plunger 51. In this connection, the conical taper at the cylinder end 56 is of importance because it conducts air bubbles perforce to the outlet connection 57.

During nonuse of the filled or partially filled device, the outlet extension 57 can be sealed by a cap; in the illustrated example of a threaded coupling of the connecting member 58 with the outlet extension 57, this can be done by a screw cap (not shown).

The connecting member 58 contains a constricted or throttle zone which, in the illustrated embodiment, is constituted by a glass capillary 64 embedded in the synthetic resin part 58 and which determines the flow rate in conjunction with the gas pressure.

In a version (not shown) of the connecting member 58, the capillary 64 is bridged by a shunt (bypass) with a valve offering the delivery possibilities (bolus) discussed hereinabove in connection with FIG. 2. A corresponding bypass can analogously also be included in the embodiments of FIGS. 1, 4 and 5.

In the device according to FIG. 4, the cylinder 70 with the outlet connection 71 and the plunger 72 are parts of a commercially available plunger-type or ampoule-type syringe, the plunger 72 being provided, on its side facing away from the outlet connection 71, with a threaded hole (not illustrated) so that the plunger can be retracted, as mentioned above, with the cylinder lid 74 having been removed, by means of a handle equipped with a threaded pin in order to fill the cylinder 70 with infusion fluid. The lid contains, in coaxial arrangement, a galvanic cell 76 generating the gas and designed as a button cell according to DOS 3,532,335 and under the load of a resistor 77, and a pressure relief valve 80. The resistor 77 is connected directly to one pole of the button cell 76 and by way of a contact spring 78 to the other pole. In this arrangement, an insulating shim (not shown) is placed between the button cell 76 and the contact spring 78, this shim projecting at the periphery of the lid 74 where the shim can be seized and pulled out in order to close the circuit and to activate the cell 76 before the lid 74 is mounted at the cylinder and the device is put to use. For the same purpose, a contact can also be provided which closes automatically when the lid 74 is placed against the cylinder 70, and which opens when the lid is removed again.

The cell 76 need not necessarily be exchangeable; it can form a unit intended for a single usage together with the lid 74 (and the pressure relief valve 80). Such units with pressure relief valves 80 set to different pressures can be designed in differing colors. This also holds true for connecting members with capillaries of differing widths.

The cylinder 70, as mentioned above, can be filled respectively for repeated use or can be filled at the factory and intended for one-time usage, in which case the outlet connection 71 is to be equipped with a removable seal or is to be penetrated by a hollow needle attached to the connecting member 82, as mentioned previously in conjunction with FIG. 1.

Likewise, the cylinder 70 with the plunger 72 and the lid 74 containing the cell 76 and the pressure relief valve 80 can be a unit for one-time use filled at the factory with infusion fluid; in this case, the lid 74 can be nondetachably joined to the cylinder 70 and is to be designed so that the previously mentioned insulating shim (in a deviation from the arrangement of the cell 76 in FIG. 4) projects from the part of the lid extending out of the cylinder 70 and is suitably secured against inadvertent pulling out.

In the connecting member 82, upstream of the capillary 83, a filter 84 is located which retains particles that may be present in the infusion fluid and could clog the capillary 83. This filter 84 and the other details described in connection with FIG. 4 are also analogously usable in the other embodiments of the infusion device, and this also holds true conversely.

The preferred embodiment of the infusion device shown in FIGS. 5-7 consists of an ampoule 101 equipped with a plunger 100, of an insert head 102 fashioned as a lid for the rear end of the ampoule, and a connection unit comprising a throttling means 103 and a catheter 104. For filling the ampoule 101 with the infusion fluid, a retraction stem 106 provided with a thread 105 at the lower end, and a connection unit 107 with cannula 108 are provided.

The ampoule 101 is a commercially available cartridge-needle unit, the frontal end of which is provided with a connecting Luer's syringe 109, and housing the likewise commercially available plunger 100 consisting of a rubber stopper 110 with an insert 111 countersunk into the stopper and having a blind threaded hole. In the rearward end of the ampoule, a mounting sleeve 112 for the insert head 102 is disposed, the outer wall of this sleeve being tightly welded to the ampoule wall. The rearward portion of the sleeve has a smooth inner wall and a collar 113 resting on the ampoule flange; the forward portion has an internal thread 114 for the insert head and an abutment 115, projecting annularly inwardly, for the plunger 100.

The insert head 102 has a head section 117 provided with a knurled zone, the diameter of this head section being larger than that of the ampoule 101, and a screw section 119 inserted from the bottom in the head section and equipped with an outer thread 118, an advancing unit for the beginning of the plunger advancement and a galvanic button cell according to DOS 3,532,335 for further plunger advancement being arranged in this screw section.

In order to regulate the gas pressure produced by the button cell 120, a pressure relief valve 121 is located in the head section 117 and communicates through a connecting duct with the button cell. The outlet of this valve terminates in an exit at the periphery of the head section 117. The exit is sealed by a bursting disk 122 which latter ruptures when the pressure relief valve 121 responds and thus indicates the operability of the valve.

The pole terminals (anode and cathode) of the button cell 120 are connected to each other via a contact tongue 123 and a contact spring 124 through a resistor 126 arranged on the underside of a printed circuit board 125. As illustrated in FIG. 5, an insulating shim 128 constituting a safety element is pushed through a slot 127 of the insert head 102 between the pole terminal of the button cell 120 and the contact spring 124; this shim protrudes laterally from the insert head 102 to such an extent that it can be conveniently seized by hand, and the insert head can be introduced into the rearward end of the ampoule only after the shim 128 has been pulled out and thus the button cell 120 has been activated.

The feeding unit comprises a tank-shaped part 130 open in the downward direction and equipped with a gas passage in the tank bottom; a push rod 131 projects into this part. The push rod 131 is hollow, closed at its lower end 134, and provided at its upper, open end with a collar 132 adapted to the inner wall of the tank. Between the tank bottom 133 and the push rod bottom 134, a compression spring 136 is clamped into place, this spring extending around a pin 135. (The pin 135 is included for reasons of reducing the air space, as will be discussed hereinbelow.) The push rod 131 is supported so that it can be reciprocated within an extension 137 between a position wherein the collar 132 abuts against the annularly inwardly projecting extension 137 of the screw section 119 and a position wherein the collar 132 abuts against the tank bottom 133. The push rod is in the former position prior to insertion of the insert head 102 (FIG. 5), in the latter position directly after threading the insert head 102 into the mounting sleeve 112 (FIG. 7).

An O-ring 138 at the periphery of the insert head 102 seals the latter during insertion at the mounting sleeve 112 so that the gas produced by the cell cannot escape. The O-ring 138 is disposed on the upper, threadless periphery of the screw member 119 and is secured against upward sliding by means of a step 116 formed by the head member 117.

The throttle device 103 has a cylindrical housing provided with a connection member on the inlet side which is adapted to the connecting Luer's syringe 109 and with a connection member on the outlet side which is adapted to a connecting Luer's syringe of the catheter 104; subsequently to the outlet duct of the connection member on the inlet side, a filter 139 and a capillary tube 140 are arranged in this cylindrical housing. The filter 139 is a commercially available medicine filter, the pore width of which is smaller than the inner diameter (40 micrometers) of the capillary tube 140 so that the latter cannot be clogged. The filter 139 and the capillary tube 140 are compressed, with O-rings 141 located at both filter ends, between two end walls of the cylindrical housing so that the infusion fluid flows reliably through the filter and the capillary tube.

In order to fill the ampoule 101 with the infusion fluid, the retraction stem 106, provided with the external thread 105 at the front, is threaded into the blind threaded bore of the insert 111 of plunger 100 and the connection unit 107 with the cannula 108 is placed on the connecting Luer's syringe 109 so that the ampoule 101 can be filled in the usual way. The ampoule 101 must be completely filled up, which is ensured by the stop 115 of the mounting sleeve 112 against which the plunger 100 abuts after a complete filling.

Once the ampoule 101 has been filled, the retraction stem 106 is threaded out of the plunger 100, and the connection unit 107 is removed from the Luer's syringe 109. The throttle means 103 is tightly connected to the catheter 104 at the outlet side and to the Luer's syringe 109 on the inlet side. Thereafter, the insulating shim 128 is pulled out of the insert head 102, and the latter is inserted in the ampoule 101 from the rear and threaded, with the external thread 118 of its screw member 119, into the internal thread 114 of the mounting sleeve 112.

After the insulating shim 128 has been pulled out, the circuit is closed between anode and cathode of the cell 120 via the resistor 126, but the cell begins gas production only once the oxygen in the air surrounding the cell has been used up, and buildup of gas pressure also requires some time, so that the operating gas pressure is built up only after one-half to one hour. (In the embodiment, the air spaces are kept to a minimum size, inter alia by insertion of the pin 135, yet the buildup of operating gas pressure requires the aforementioned time period.) Although the operating gas pressure is built up only gradually, the advance of the plunger begins, for the reasons explained hereinbelow, directly after threading the insert head 102 into the ampoule, and with it the delivery of the infusion fluid. This is important inasmuch as immediate delivery can be necessary or at least desirable for the patient, and the patient, when delivery is not forthcoming, would additionally assume a disturbance in functioning of the device.

During the threading of the screw member 119 into place, the O-ring 138 is forced, by the shoulder 116, into the smooth cylindrical wall of the upper portion of the mounting sleeve 112 and slides therealong downwardly so that the air between the O-ring 138 and the plunger 100 is compressed. The air space underneath the O-ring 138 is in communication via the threads 114, 118 and the gaps between the mounting sleeve 112, the screw member 119, the push rod 131, the feeding member 130 with the passage in the tank bottom 133, and the printed circuit board, with the air space around the cell 120, as well as with the inlet of the pressure relief valve 121 via the connecting duct. The arrangement of the O-ring 138, i.e. the distance along which the O-ring 138 is moved along the mounting sleeve, is chosen in relation to the air spaces so that the compressed air attains an excess pressure at which the pressure relief valve 121 responds so that the bursting disk 122 ruptures and thereby the functioning of the pressure relief valve 121 is indicated.

Upon the beginning of the threaded insertion of screw member 119, the push rod 131 is urged downwardly by the spring 136 and its collar 132 rests on the extension 137. During continued threading engagement, the (threadless) push rod 131 enters the blind threaded bore of the insert 111 of plunger 100. Since the infusion fluid can be discharged only very gradually through the filter 139 and the capillary tube 140, the plunger 100 (additionally held by static friction in the ampoule 101) is retained against the bias of the spring 136 by the liquid pressure of the infusion fluid, and the push rod 131 is thus moved against the spring bias upwards into the position shown in FIG. 7.

The initial pressure of the compressed air now acts on the plunger 100 and also—via the push rod 131—the force of the spring 136, so that the plunger 100 is advanced directly after threading the insert head 102 into place, in spite of the fact that the gas pressure has not as yet been built up, and the infusion fluid begins to flow out through the throttle means 103 and the catheter 104.

The spring 136 is dimensioned so that the pressure exerted by the plunger 100 on the infusion fluid at the beginning of advancement due to spring bias is approximately of the same magnitude as the pressure exerted on the infusion fluid by the plunger 100 with completely built-up gas pressure (with the spring being ineffective), and so that the plunger 100 during the buildup of gas pressure by the cell 120 is advanced at a constantly decreasing spring force so that the result is an almost constant plunger advance, due to the superposition of decreasing spring force and increasing gas pressure, and a correspondingly constant delivery rate results which, with the gas pressure being fully built up, is maintained further solely by this gas pressure.

Directly after threaded engagement of the insert head 102, the plunger advance is, for a brief time, larger than after complete buildup of gas pressure, since the spring force as well as the compressed air act on the plunger 100; this is desirable since first the device 103 and the catheter 104 must be filled with the infusion fluid. With completely built-up gas pressure, the collar 132 of the push rod 131 abuts against the extension 137 so that the spring force no longer acts on the plunger 100 which latter moves away from the push rod 131 on account of the gas pressure. The resistor 126 and the pressure relief valve 121 take care thereafter that the gas pressure generated by the cell remains constant. The resistor 126 is dimensioned so that the cell supplies an adequate amount of gas to maintain the operating gas pressure required for the desired delivery rate; the excess pressure at which the pressure relief valve 121 is opened is set to be higher by a tolerance of about 0.2 bar than the operating gas pressure.

The inner diameter of the capillary tube 140 is dimensioned to be so small, preferably 40 micrometers, that the traversing infusion fluid has to overcome a high (frictional) resistance which is so high that the friction of the plunger 100 and the dermal counterpressure of the patient are negligible as compared thereto. As a result, fluctuations in plunger friction and in dermal counterpressure have practically no effect on the delivery rate (infusion rate), and it is possible to operate at a high operating gas pressure ensuring a reliably constant advancement rate of the plunger. It has been found that the delivery rate (infusion rate) is approximately proportional to the gas operating pressure and indirectly proportional to the viscosity and to the length of the capillary tube, but depends with the fourth power on the internal diameter of the capillary tube 140; for this reason, the inner diameter must be maintained very accurately in order to ensure the desired infusion rate.

Depending on medicament and indication, varying delivery rates of, for example, 0.5–4 ml/h, and differing ampoule contents of, for example, 10–100 ml are suitable. The components illustrated in FIG. 5 can be utilized as a kit for the assembly of infusion devices having varying infusion rates. The infusion rate is determined—with equally dimensioned throttle means 103 (same internal diameter of the capillary tube) and identical cell 120—solely by resistor 126 since the gas flow increases in proportion to the electrical current. The kit accordingly consists of a set of ampoules 101 having identical or differing volume, and a set of insert heads 102 equipped, for differing infusion rates, with differing resistors 126 and being identified correspondingly. The remaining accessories for the insert head 102 are adapted to the respective resistor 126 and, respectively, the gas operating pressure associated with this resistor, namely the setting of the pressure relief valve 121 and, if necessary, also the spring 136 governing for the initial pressure, as well as the arrangement of O-ring 138 determining for the air compression. For an infusion rate of 1 ml/h, the resistor is to be dimensioned, for example, in such a way that a gas operating pressure of 1 bar is maintained, for an infusion rate of 3 ml/h, a pressure of about 1.5 bar is maintained. The throttle means 103 with the catheter 104 and the retraction stem 106 as well as the connection unit 107 can be of identical structure for all infusion devices; in this context—as mentioned previously—the internal diameter of the capillary tube 140 must be very accurately maintained.

For very high infusion rates, it is also possible to arrange, in place of one cell 120, several cells 120 in the insert head 102.

We claim:

1. A medical infusion device, comprising
   a chamber for accommodation of an infusion liquid,
   said chamber having an outlet for the liquid at one end thereof and a movable wall at the opposite end for varying the size of said chamber and adapted to discharge liquid from said chamber through said outlet,
   means connected to seal the opposite end of said chamber outwardly of said moveable wall,
   a gas generating galvanic cell connected between said moveable wall and said means sealing the opposite end of said chamber,
   and a load resistor connected across said cell,
   whereby said cell delivers a constant quantity of gas pressure per unit of time determined by said load resistor to advance said moveable wall and discharge liquid through said outlet.

2. A medical infusion device as set forth in claim 1, in which said means connected to seal the opposite end of said chamber comprises an insert head attachable in gas tight relation to said opposite end of said chamber, and said gas generating galvanic cell and resistor located in said insert head.

3. A medical infusion device as set forth in claim 2, including a pressure relief valve connected in said insert head to regulate the gas pressure therein produced by said gas generating galvanic cell.

4. A medical infusion device as set forth in claim 3, including a passage in said insert head having an exit end exterior of said insert head, said pressure relief valve connected in said passage, and a burstable seal sealing said exit end and adapted to rupture when said pressure relief valve operates.

5. A medical infusion device as set forth in claim 2, in which said chamber comprises an ampoule having an inner cylindrical wall on said opposite end rearwardly of said moveable wall, said moveable wall comprising a moveable piston, a sealing ring between said inner cylindrical wall and said insert, whereby upon attachment of said insert head to the opposite end of said ampoule air compressed between said sealing ring and said piston advances said piston by the initial pressure of the compressed air directly after connection of said insert head.

6. A medical infusion device as set forth in claim 5, including a spring in said insert head positioned to act on the rear of said piston when said insert head is connected to said opposite end of said ampoule, and said spring having an operating path dimensioned so that said spring advances the piston during the buildup of gas pressure by said cell.

7. A medical infusion device according to claim 6, in which said spring (136) is dimensioned so that the pressure exerted by the piston (100) on the infusion fluid at the beginning of the advance on account of the spring force and optionally on account of the compressed air is at least approximately as high, or higher, as or than the pressure exerted by the piston (100) on the infusion fluid after the gas operating pressure has been completely built up, without a spring force.

8. A medical infusion device as set forth in claim 1, in which said load resistor is a variable resistor.

9. A medical infusion device as set forth in claim 1, including a contact connected in series between said resistor and said cell, means maintaining said contact in an open position in the inoperative condition of said device and closing said contact to complete a circuit between said cell and resistor in the operative condition of said device.

10. A medical infusion device as set forth in claim 9, including an opening through said means connected to seal in alignment with said contact, said contact is a spring contact, and said means maintaining said contact in an open position comprising an insulated member extending through said opening in said means connected to seal and maintaining said spring contact in an open position when said means connected to seal is disconnected from said opposite end of said chamber.

11. A medical infusion device as set forth in claim 1, including a liquid throttle member connected to said outlet of said chamber for the infusion liquid to be administered to a patient.

12. A medical infusion device according to claim 11, including a filter (84; 139) arranged between the outlet (10; 109) and the throttle member (83; 140), the pore width of this filter being smaller than the width of the throttle member (83; 140).

13. A medical infusion device as set forth in claim 1, including a connection unit connected to said outlet of said chamber for the infusion liquid, a filter in said connection unit adjacent said outlet, and a throttle member in said connection unit for the infusion liquid formed by a capillary tube.

* * * * *